(12) United States Patent
Verleye et al.

(10) Patent No.: US 8,338,410 B2
(45) Date of Patent: Dec. 25, 2012

(54) NEUROPROTECTIVE COMPOUNDS AND PHARMACEUTICAL COMPOSITIONS COMPRISING THEM

(75) Inventors: Marc Verleye, Remy (FR);
Marie-Emmanuelle Le Guern, Compiegne (FR); Philippe Girard, Margeny-les-Compeigne (FR); Jean-Marie Gillardin, Jonquieres (FR); Laurence Berthon-Cedille, Ricquebourg (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 1276 days.

(21) Appl. No.: 11/488,187

(22) Filed: Jul. 18, 2006

(65) Prior Publication Data
US 2007/0167446 A1    Jul. 19, 2007

(30) Foreign Application Priority Data
Jul. 19, 2005   (FR) .................................. 05 07648

(51) Int. Cl.
*A61K 31/535* (2006.01)
*A01N 43/16* (2006.01)

(52) U.S. Cl. ...................... 514/229.8; 514/459; 514/460

(58) Field of Classification Search ............... 514/229.8, 514/459, 460
See application file for complete search history.

(56) References Cited

U.S. PATENT DOCUMENTS

| | | | |
|---|---|---|---|
| 8,110,569 B2 * | 2/2012 | Putman et al. ............. | 514/230.5 |
| 2004/0209904 A1 | 10/2004 | Dunn et al. | |
| 2008/0038331 A1 * | 2/2008 | Putman et al. ................ | 424/451 |

FOREIGN PATENT DOCUMENTS

| | | |
|---|---|---|
| DE | 34 39 055 | 4/1986 |
| WO | WO-2004/035000 | 4/2004 |

OTHER PUBLICATIONS

Girard et al. "Etifoxine improves peripheral nerve regeneration and functional recovery" PNAS Dec. 23, 2008, vol. 105, No. 51, pp. 20505-20510.*
Database, Embase, Elsevier Science Publishers, Amsterdam, NL, 1985, Kruse et al "Etifoxine: Evaluation of its anticonvulsant profile in mice in comparison with sodium valproate, phenytoin and clobazam" & Arzneimittel-Forschung/Drug Research 1985 Germany, vol. 35, No. 1, 1985, pp. 133-135.
Database, Embase, Elsevier Science Publishers, Amsterdam, NL, 1986, Kruse et al; "Potentiation of clobazam's anticonvulsant activity by etifoxine, a non-benzodiaepine tranquilizer, in mice. Comparison studies with sodium valproate" &Arzneimittel-Forschung/Drug Research 1985 Germany, vol. 36, No. 9, 1986, pp. 1320-1322.
Doongaji et al "A preliminary study o etafenoxine"; Jan. 1976; pp. 37-43; vol. 22, No. 1, Journal of Postgraduate medicine.
Gratton et al "Proceedings: etafenoxin in the treatment of neurosis—an uncontrolled clinical study" Jan. 1976; pp. 16-18; vol. 12, No. 1, Psychopharmacology Bulletin.

* cited by examiner

*Primary Examiner* — Renee Claytor
(74) *Attorney, Agent, or Firm* — B. Aaron Schulman, Esq.; Stites & Harbison PLLC

(57) ABSTRACT

This invention relates to the use of at least one compound of the following formula (I):

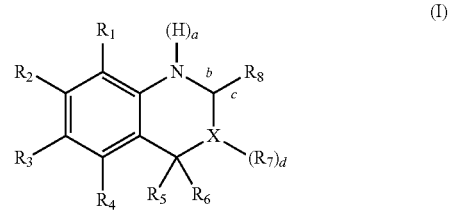

or its pharmaceutically acceptable salts,
for the preparation of a medicinal compound having neuroprotective activity intended to prevent or treat neurone deteriorations.

9 Claims, 9 Drawing Sheets

NEUROPROTECTIVE COMPOUNDS AND PHARMACEUTICAL COMPOSITIONS COMPRISING THEM

This invention relates to the use of neuroprotective compounds in the context of the prevention of the treatment of neuronal deteriorations due to diseases of the nervous system.

Neuronal deterioration, in particular neurone death, plays an essential part in almost all diseases involving acute or chronic neuronal degeneration. It is thought that many neurochemical modulators are involved in the occurrence of lesions in the nervous system. For example, in epilepsy neurotransmission with excess glutamate, the deterioration of inhibition associated with GABA and changes in acid-base equilibrium can result in a series of events leading to neuronal damages and cell death.

Several biochemical pathways resulting in neurone death have been elucidated in recent years. One of the most documented cases relates to the excitotoxicity of glutamate. This neurotransmitter amino acid is released excessively for example in the case of ischaemia, and this, through excessive activation of its neuronal receptors, gives rise to an inflow of calcium ions into the neurones and leads to cell death through necrosis or apoptosis.

By definition, neuroprotection is an activity whose consequence is the preservation, recovery, cure or regeneration of the nervous system, its cells, its structure and function (Vajda et al. (2002) J Clin Neurosci. 9:4-8). As indicated in FIG. 9, neuroprotection acts in particular on the processes leading to neurone death.

The presumed mechanisms of neurone death, which are both complex and varied, such as oxidative stress, mitochondrial dysfunction, protein aggregation, apoptosis and inflammation (Youdim et al. (2005), TIPS 26:27-35), suggest that neuroprotective treatments act at several levels both neurologically and biochemically (Youdim M B et al. (2005) J. Neural. Transm. 112:519-537) (Sellal et al. (2005) Therapie, 60:89-107).

Thus in the context of the treatment of cerebral ischaemic accidents it has been demonstrated that many agents which inhibit some stages in the process of neurone death, such as glutamate antagonists, anti-inflammatory agents, ion channel modulator agents, anti-free-radical agents, or again GABA antagonists, have a neuroprotective action in animals.

However the clinical trials which have been carried out hitherto have not been able to confirm the potential of these compounds as neuroprotective agents in man.

One object of this invention is therefore to provide pharmaceutical compositions having neuroprotective effectiveness greater than that of the compositions already known.

This invention derives in particular from the discovery by the Inventors that etifoxine and desethyl-etifoxine have a neuroprotective action in animals in vitro and in vivo.

This invention thus relates to the use of at least one compound having the following formula (I):

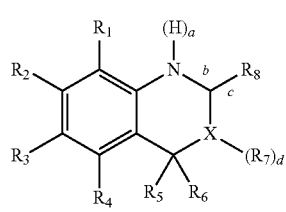

in which:
a represents 0 or 1,
b represents a single bond or a double bond,
c represents a single bond or a double bond,
d represents 0 or 1,
X represents an oxygen or nitrogen atom, provided that when X represents an oxygen atom then d has the value of 0 and when X represents a nitrogen atom then d has the value of 1,
$R_1$, $R_2$, $R_3$, and $R_4$, which are the same or different, represent a hydrogen atom, a halogen atom, in particular selected from F, Cl, Br, or I, a hydroxyl group, or an alkoxyl group having 1 or 2 carbon atoms,
$R_5$ and $R_6$, which are the same or different, represent a hydrogen atom, an alkyl or cycloalkyl group having 1 to 6 carbon atoms, or an aryl group having 6 carbon atoms in which the aromatic ring may be substituted by one or more halogen atoms or one or more hydroxyl groups, alkoxyl having 1 or 2 carbon atoms, trifluoromethyl or nitro,
$R_7$ represents a hydrogen atom, a hydroxyl group, or an alkyl or hydroxyalkyl group having 1 to 3 carbon atoms,
$R_8$ represents an oxygen atom or a —$NR_9R_{10}$ group, $R_9$ and $R_{10}$, which are the same or different, representing a hydrogen atom, a hydroxyl group, or an alkyl or hydroxyalkyl group having 1 to 3 carbon atoms, provided than when $R_8$ represents an oxygen atom then a has the value 1, b represents a single bond and c represents a double bond and that when $R_8$ represents a —$NR_9R_{10}$ group then a has the value 0, b represents a double bond and c represents a single bond,
or their pharmaceutically acceptable salts, for the preparation of a medicinal product having neuroprotective activity which is intended to prevent or treat neurone deteriorations.

By "neuroprotective activity" is meant an action which has the consequence of the preservation, recovery, cure or regeneration of the nervous system, its cells, its structure and function (Vajda et al. (2002) J Clin Neurosci 9:4-8).

By "neurone deteriorations" is meant the microscopic lesions in cells observed in various neurological diseases. These lesions may in particular be in the nature of ischaemic lesions, atrophic lesions, neuronal loss, intracytoplasmic or intranuclear inclusions, neurofibril or granulo-vacuolar degeneration.

By way of example neuronal lesions observed in Alzheimer's disease associate neurofibril degeneration with the loss of synapses in the hippocampus and adjacent regions of the temporal lobe, intracortical foci of neuronal extensions which are thickened both axonally and dendritically (neuritis), and granulo-vacuolar degeneration. The ischaemic lesions observed in the course of ischaemic vascular accidents associate a dark core with a very basophilic and shrunken cytoplasm. Neurodegenerative diseases accompany lesions of the neuronal atrophy type with depopulation of areas characteristic of the disease (Augustinack et al. (2002); Acta Neuropathol. 103:26-35)—(Harrison—Arnett Blackwell Ed 1995)—(Cambier—Masson Ed 2000).

In a particular embodiment of the use as defined above, neurone deteriorations are associated with diseases selected from the list comprising:
epilepsy,
ischaemic or hemorrhagic cerebral vascular accidents,
neurodegenerative diseases, such as Charcot-Marie-Tooth disease or Friedreich disease,
phacomatoses, in particular neurofibromatoses,
neuropathic diseases, such as deficiency neuropathies, in particular of the alcoholic kind, toxic or drug-induced neuropathies, particularly by vincristine, neuropathies associated with a metabolic disturbance such as diabetes, neuropathy associated with an inflammatory process, in particular *Guillain-Barre* syndrome, infectious neuropathic diseases, in particular *Herpes zoster*, and radiculo-neuropathic diseases, paraneoplastic polyneuritis, multiple sclerosis, amyotrophic lateral sclerosis, schizophrenia, depression, brain tumours, Parkinson's disease, and dementias, such as Alzheimer's disease, Pick's disease or vascular dementia.

The compounds of formula (I) defined above may easily be synthesised using the teaching in French patent no. 1 571 287.

Pharmaceutically acceptable salts according to the invention will be obvious according to those skilled in the art, in particular the hydrochloride salts of compounds of formula (I) according to the invention are preferred.

As understood here, this invention also relates to the use as defined above of optically active forms of the compound of formula (I), such as the following enantiomers (when $R_5$ and $R_6$ are different):

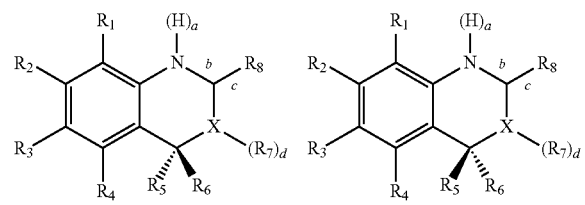

or their mixtures, in particular their racemic mixture.

In a particular embodiment, the invention relates to the use as defined above of a compound of formula (VIII) as follows:

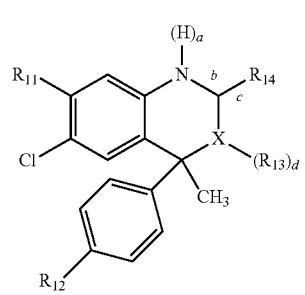

in which:

a represents 0 or 1, b represents a single bond or a double bond, c represents a single bond or a double bond, d represents 0 or 1, X represents an oxygen or nitrogen atom, provided that that when X represents an oxygen atom then d has the value 0 and when X represents a nitrogen atom then d has the value 1, $R_{11}$ and $R_{12}$, which are the same or different, represent —H or —OH, $R_{13}$ represents —H or a —$CH_2$—$CH_3$ group, $R_{14}$ represents an oxygen atom or a —$NH_2$ or —NH—$CH_2$—$CH_3$ group, provided that when $R_{14}$ represents an oxygen atom then a has the value of 1, b represents a single bond and c represents a double bond, and that when $R_{14}$ represents a —$NH_2$ or —NH—$CH_2$—$CH_3$ group then a has the value of 0, b represents a double bond and c represents a single bond.

This invention also relates to the use as defined above of optically active forms of the compound of formula (VIII), such as the following enantiomers:

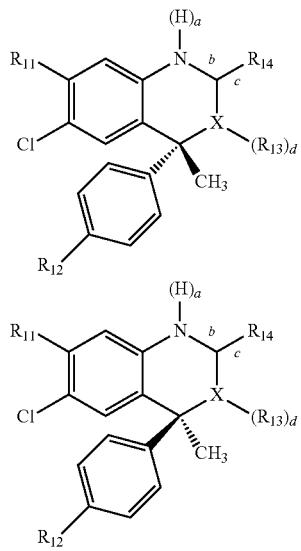

or their mixtures, in particular their racemic mixture.

In a particular embodiment, the invention relates to the use as defined above of a compound of the following formula (II):

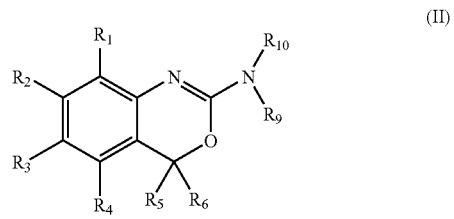

in which $R_1$, $R_2$, $R_3$, $R_4$, $R_5$, $R_6$, $R_9$ and $R_{10}$ are as defined above.

This invention also relates to the use as defined above of optically active forms of the compound of formula (II), such as the following enantiomers (when $R_5$ and $R_6$ are different):

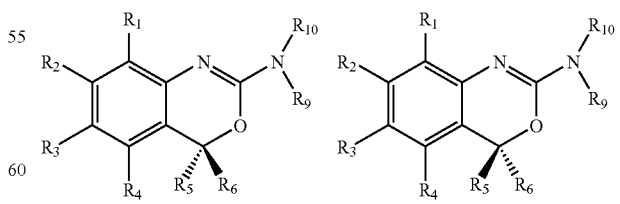

or their mixtures, in particular their racemic mixture.

In another particular embodiment, the invention relates to the use as defined above of compounds of the following formulae (III) and (IV):

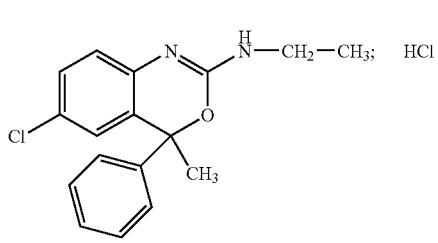

(III)

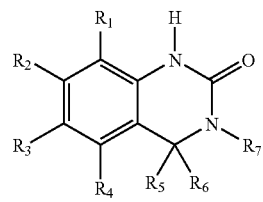

(V)

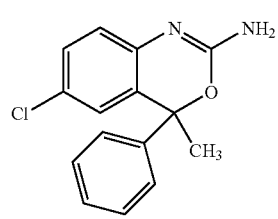

(IV)

in which $R_1$, $R_2$, $R_3$, $R_5$, $R_6$, and $R_7$ are as defined above.

This invention also relates to the use as defined above of optically active forms of the compound of formula (V), such as the following enantiomers (when $R_5$ and $R_6$ are different):

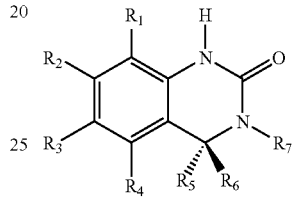 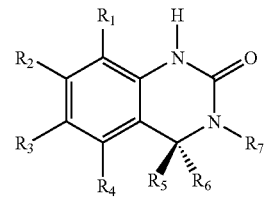

The compound of formula (III) is etifoxine, or 6-chloro-2-ethylamino-4-methyl-4-phenyl-4H-[3,1]benzoxazine hydrochloride.

The compound of formula (IV), desethyl-etifoxine or 2-amino-6-chloro-4-methyl-4-phenyl-4H-[3,1]benzoxazine, is a metabolite of etifoxine.

This invention also relates to the use as defined above of optically active forms of the compound of formula (III), such as the following enantiomers:

or their mixtures, in particular their racemic mixture.

In another particular embodiment the invention relates to the use as defined above of compounds of the following formulae (VI) and (VII):

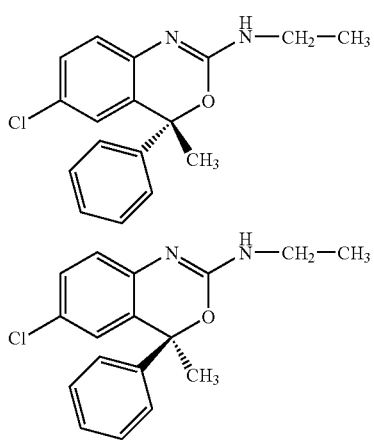

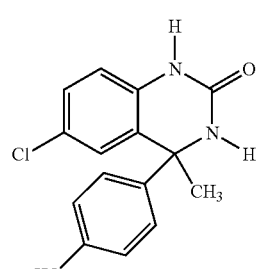

(VI)

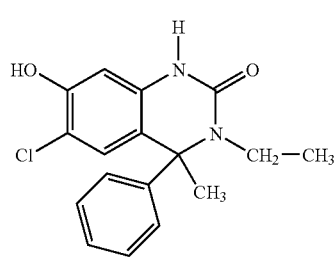

(VII)

or their mixtures, in particular their racemic mixture, particularly in their hydrochloride form, and the use as defined above, of optically active forms of the compound of formula (IV), such as the following enantiomers:

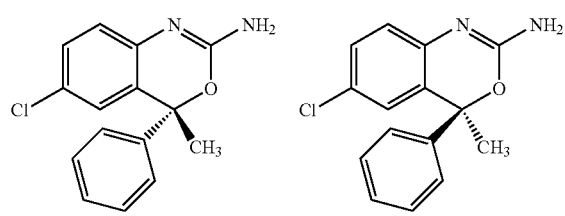

or their mixtures, in particular their racemic mixture.

In another embodiment, the invention relates to the use as defined above of a compound of the following formula (V):

The compounds of formula (VI) (6-chloro-4-(4-hydroxyphenyl)-4-methyl-3,4-dihydro-1H-quinazolin-2-one) and (VII) (6-chloro-3-ethyl-7-hydroxy-4-methyl-4-phenyl-3,4-dihydro-1H-quinazolin-2-one) are metabolites of etifoxine.

This invention also relates to the use as defined above of optically active forms of the compound of formula (VI), such as the following enantiomers:

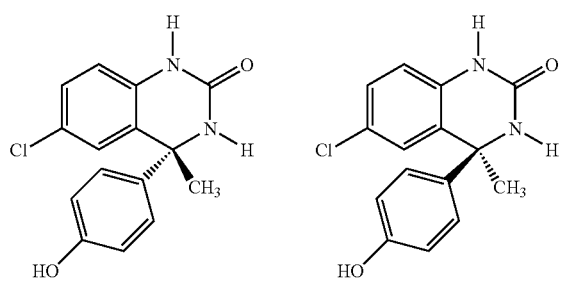

or their mixtures, in particular their racemic mixture, and the use as defined above of optically active forms of the compound of formula (VII), such as the following enantiomers:

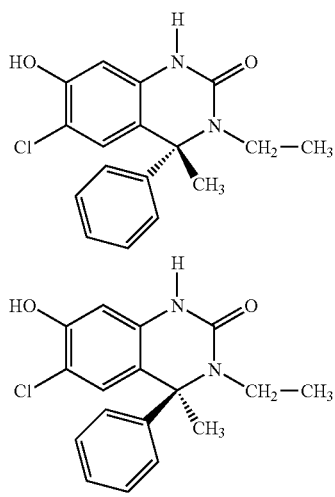

or their mixtures, in particular their racemic mixture.

In a particular embodiment of the invention, the medicinal product defined above is suitable for administration to an individual in need thereof of a unit dose of from approximately 50 mg to approximately 1500 mg, in particular from approximately 150 to 200 mg of the compound as defined above.

In another particular embodiment of the invention, the medicinal product defined above is suitable for administration to an individual in need thereof of a dose of from approximately 50 mg/d to approximately 1500 mg/d, in particular from approximately 150 mg/d to approximately 200 mg/d, of the compound as defined above.

According to a preferred embodiment of the invention, the medicinal product defined above is suitable for oral administration.

In accordance with another preferred embodiment of the invention, the medicinal product defined above takes the form of a powder, patches, capsules or sachets.

In a particular embodiment of the invention, the compound defined above is associated with at least one additional compound which is intended to prevent or treat the diseases defined above.

This invention also relates to a pharmaceutical composition comprising as the active ingredient:
at least one compound of formula (I) as defined above or its pharmaceutically acceptable salts, and
at least one additional compound intended to prevent or treat diseases selected from the group comprising:
epilepsy,
ischaemic or hemorrhagic cerebral vascular accidents,
neurodegenerative diseases, such as Charcot-Marie-Tooth disease or Friedreich disease,
phacomatoses, in particular neurofibromatoses,
neuropathic diseases, such as deficiency neuropathy, in particular of the alcoholic kind, toxic or drug-induced neuropathy, particularly by vincristine, neuropathy associated with a metabolic disturbance such as diabetes, neuropathy associated with an inflammatory process, in particular *Guillain-Barre* syndrome, infectious neuropathic diseases, in particular *Herpes zoster*, and radiculoneuropathic diseases,
paraneoplastic polyneuritis,
multiple sclerosis,
amyotrophic lateral sclerosis,
schizophrenia,
depression,
brain tumours,
Parkinson's disease, and
dementias, such as Alzheimer's disease, Pick's disease or vascular dementia,
in association with a pharmaceutically acceptable vehicle.

This invention also relates to products containing:
at least one compound of formula (I) as defined above or its pharmaceutically acceptable salts, and
at least one additional compound intended to prevent or treat diseases selected from the list comprising:
epilepsy,
ischaemic or hemorrhagic cerebral vascular accidents,
neurodegenerative diseases, such as Charcot-Marie-Tooth disease or Friedreich disease,
phacomatoses, in particular neurofibromatoses,
neuropathic diseases, such as deficiency neuropathy, in particular of the alcoholic kind, toxic or drug-induced neuropathy, particularly by vincristine, neuropathy associated with a metabolic disturbance such as diabetes, neuropathy associated with an inflammatory process, in particular *Guillain-Barre* syndrome, infectious neuropathic diseases, in particular *Herpes zoster*, and radiculoneuropathic diseases,
paraneoplastic polyneuritis,
multiple sclerosis,
amyotrophic lateral sclerosis,
schizophrenia,
depression,
brain tumours,
Parkinson's disease, and
Dementias, such as Alzheimer's disease, Pick's disease or vascular dementia,
as a combination product for separate, simultaneous or sequential use to prevent or treat neurone deteriorations associated with these diseases.

In a preferred embodiment of the invention the additional compound defined above is selected from the list comprising:
an antiepileptic agent, in particular:
Valproic acid,
Barbiturates,
Carbamazepine,
Ethosuximide,
Gabapentin,
Lamotrigine,
Stiripentol,
Tiagabine,
Vigabatrin, an anti-Parkinson's disease agent, in particular:
  a dopaminergic agent, such as:
    Levodopa associated with dopadecarboxylase inhibitor,
    Dopaminergic agonists,
  Anticholinergic agents such as:
    Biperidene,
    Trihexyphenidyl,
    Tropatepine,
  a monoamine oxidase B (IMAO B) inhibitor,
  a catechol-O-methyl transferase (COMT) inhibitor,
a compound intended for the treatment of Alzheimer's disease, in particular:
  an anticholinesterase such as:
    Donepezil,
    Galantamine,
    Rivastigmine,
  an NMDA receptor antagonist such as:
    Memantine,
a compound intended for the treatment of acute phase ischaemic CVA (cerebrovascular accidents) (Alteplase) and their sequaelae (Dihydroergocristine, Piracetam), in particular according to the type of CVA:
  Heparin,
  Aspirin,
  Nicardipine.
a compound intended for the treatment of multiple sclerosis, in particular:
  Interferon β,
  Glatiramer acetate,
  Mitoxantrone,
a compound intended for the treatment of amyotrophic lateral sclerosis, in particular:
  Riluzole,
a compound intended for the treatment of *Guillain Barre* syndrome, in particular:
  Type G human immunoglobulins,
  Tegeline,
a compound intended for the treatment of cerebral hemorrhage, in particular:
  Nimodipine,
an antidepressant, in particular:
  an imipraminic, such as:
    Anafranil,
    Clomipramine,
    Amoxapine,
    Amitriptyline,
  a selective serotonin re-uptake inhibitor, such as
    Fluoxetine,
    Paroxetine,
    Citalopram,
    Fluvoxamine,
  a selective re-uptake inhibitor of serotonin and of noradrenaline, such as:
    Venlafaxine,
    Mirtazapine,
    Tianeptine,
a compound intended for the treatment of schizophrenia, in particular:
  a psychotropic agent, such as:
    Olanzapine,
    Risperidone,
    Clozapine,
  A neuroleptic, such as
    Haloperidol,
    Pipotiazine, a compound intended for the treatment of cerebral tumours, in particular a chemotherapy agent,
a compound intended for the treatment of diabetic neuropathy, in particular a compound intended for the correction of metabolic disturbances (insulin),
a compound intended for the treatment of alcoholic polyneuritis, in particular vitamin B1.

Advantageously compounds of general formula (I) or its pharmaceutically acceptable salts are used as an adjuvant intended to increase the effects of the compounds intended for treatment of the diseases specified above, such as the additional compounds defined above.

DESCRIPTION OF THE FIGURES

FIG. 1 shows the effects of increasing concentrations of etifoxine (as the abscissa, μM) on the density of marking of neuritic extensions (as ordinate, percentage surface area marked) in the absence of glutamate (control) or in its presence (2 or 10 mM) after 6 hours incubation. Each column shows the mean±standard deviation from the mean (8 measurements per group). FGF represents the growth factor. The asterisk (*) represents $p<0.05$ in comparison with the corresponding controls (dose 0) and the hash sign (#) represents $p<0.05$ in comparison with the controls (without glutamate).

FIG. 2 shows the effects of increasing concentrations of etifoxine (as the abscissa, μM) on the density of labelling of neuritic extensions (as ordinate, percentage surface area marked) in the absence of glutamate (control) or in its presence (2 or 10 mM) after 24 hours incubation. Each column shows the mean±standard deviation from the mean (8 measurements per group). FGF represents the growth factor. The asterisk (*) represents $p<0.05$ in comparison with the corresponding controls (dose 0) and the hash sign (#) represents $p<0.05$ in comparison with the controls (without glutamate).

FIG. 3 shows the effects of increasing concentrations of desethyl-etifoxine (as the abscissa, μM) on the density of labelling of neuritic extensions (as ordinate, percentage surface area marked) in the absence of glutamate (control) or in its presence (2 or 10 mM) after 6 hours incubation. Each column shows the mean±standard deviation from the mean (8 measurements per group). FGF represents the growth factor. The asterisk (*) represents $p<0.05$ in comparison with the corresponding controls (dose 0) and the hash sign (#) represents $p<0.05$ in comparison with the controls (without glutamate).

FIGS. 4A and 4B illustrate the effects of increasing concentrations of etifoxine (as abscissa, mg/kg) administered intraperitoneally (FIG. 4A) or orally (FIG. 4B) on survival time (as ordinate, in seconds, mean±standard deviation from the mean) for mice subjected to hypobaric hypoxia induced by decreasing atmospheric pressure to 160 mmHg (9 or 10 animals per group). The asterisk (*) represents $p<0.05$ in comparison with the corresponding controls in the ANOVA statistical test.

FIGS. 5A and 5B illustrate the effects of increasing concentrations of etifoxine (as abscissa, mg/kg) administered intraperitoneally (FIG. 5A) or orally (FIG. 5B) on survival time (as ordinate, in seconds, mean±standard deviation from the mean) for mice subjected to histotoxic hypoxia induced by intraperitoneal administration of 15 mg/kg of potassium cyanide (9 to 19 animals per group). The asterisk (*) represents p<0.05 in comparison with the corresponding controls in the ANOVA statistical test.

FIGS. 6A and 6B illustrate the effects of increasing concentrations of etifoxine (as abscissa, mg/kg) administered intraperitoneally (FIG. 6A) or orally (FIG. 6B) on survival time (as ordinate, in seconds, mean±standard deviation from the mean) for rats subjected to histotoxic hypoxia induced by intraperitoneal administration of 4 mg/kg of potassium cyanide (9 or 10 animals per group). The asterisk (*) represents p<0.05 in comparison with the corresponding controls in the ANOVA statistical test.

FIGS. 7A and 7B illustrate the effects of increasing concentrations of desethyl-etifoxine (as abscissa, mg/kg) administered intraperitoneally (FIG. 7A) or orally (FIG. 7B) on survival time (as ordinate, in seconds, mean±standard deviation from the mean) for mice subjected to hypobaric hypoxia induced by decreasing atmospheric pressure to 160 mmHg (10 to 20 animals per group). The asterisk (*) represents p<0.05 in comparison with the corresponding controls in the ANOVA statistical test.

FIGS. 8A and 8B illustrate the effects of increasing concentrations of desethyl-etifoxine (as abscissa, mg/kg) administered intraperitoneally (FIG. 8A) or orally (FIG. 8B) on survival time (as ordinate, in seconds, mean±standard deviation from the mean) for rats subjected to histotoxic hypoxia induced by intraperitoneal administration of 4 mg/kg of potassium cyanide (10 animals per group). The asterisk (*) represents p<0.05 in comparison with the corresponding controls in the ANOVA statistical test.

FIG. 9 illustrates the effects of treatment for Parkinson's disease as described by Fenelon (2005) Rev. Prat. 714-716.

EXAMPLES

Example 1

Figure 1:
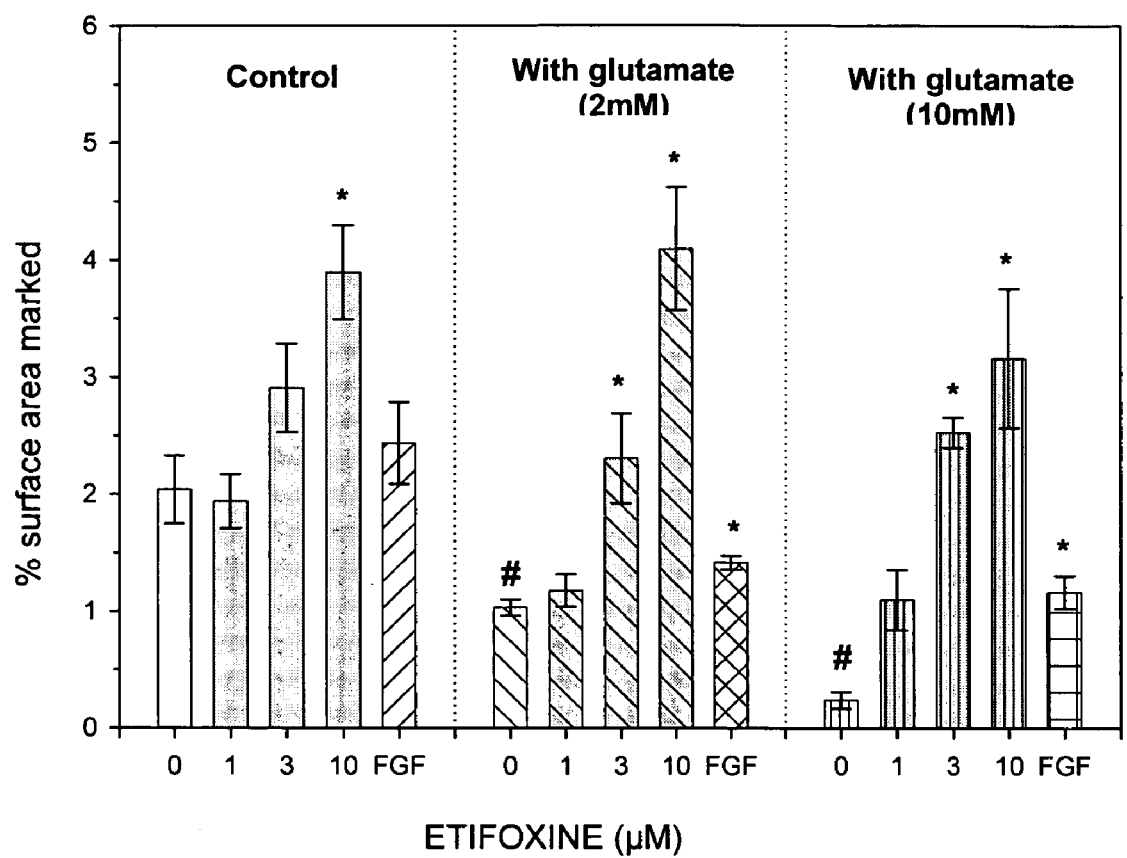
FIG. 1

Evaluation of the Neuroprotective Effects of Etifoxine in Mixed Cultures of Rat Cortical Neurones and Astrocytes in the Presence of Excess Glutamate The principle of the investigation consisted of evaluating the survival of cortical neurones in co-culture with astrocytes after the application of a neurotoxic agent, excess glutamate.

In fact glutamate is responsible for excitotoxicity (excessive activation of neuronal receptors) involved in neurone death following many disturbances including cerebral vascular accidents, epileptic crises or some neurodegenerative conditions such as Huntington's disease or amyotrophic lateral sclerosis.

Neurone survival is quantified by the density of the system of neuritic extensions marked by an anti-neurofilament antibody in the absence or presence of glutamate.

1. Material and Methods
1.1. Cell cultures
Cell type: Initial culture of cortical neurones from 14 day rat embryos and initial culture of cortical astrocytes from newborn rats.
Culture medium: DMEM-Ham F12 (Invitrogen 21331020)
  B27 2% (invitrogen 17504044)
  L-glutamine 2 mM (Invitrogen 25030024)
  Penicillin 50 UI/ml—Streptomycin 50 µg/ml (Invitrogen 15070063)
  Nerve Growth Factor 10 ng/ml (NGF, Invitrogen 13290.010)
Survival medium: MEM (Invitrogen 21090022)
  L-glutamine 2 mM (Invitrogen 25030024)
  Penicillin 50 UI/ml—Streptomycin 50 µg/ml (Invitrogen 15070063)
  Supplement N2 (Invitrogen 17502-048)
1.2 Prior Cytotoxicity
  Platelets: 96 wells
  Culture time: 8 days
  Cells/well: cortical neurones+astrocytes
  Product range: from 100 µM then ratio 3
  Replicates: 3
  Cell/product contact: 48 hours
  Evaluation parameters: microscopic observation and MTT hydrolysis.
  MTT: 3-(4,5-dimethylthiozol-2-yl)-2,5-diphenyltetrazolium bromide
1.3 Treatment and Analysis of the Network of Extensions Marked with Antineurofilament Antibody The cortical neurones were obtained from the cortex of 14 day rat embryos cultured in platelet culture medium 96 and then in a stove at 37° C. and 5% $CO_2$ with saturated humidity. After 2 days culture astrocytes obtained from newborn rat cortex were seeded in the wells (in a ratio of 1 astrocyte to 4 neurones). After 10 days culture the mature neurones synthesised neurofilaments (structural protein specific to mature neurones); in addition to this these neurones expressed functional receptors to glutamate on their surfaces and could therefore be intoxicated.

On the $12^{th}$ day of culture the medium was replaced by survival medium with or without etifoxine in 3 concentrations and the neurones were or were not intoxicated with glutamate (Sigma G1501) at a strength of 2 mM and 10 mM. Each culture condition was applied to 4 wells. The cultures were incubated for 2 periods (6 and 24 hours).

A positive control was carried out in the survival culture medium containing Nerve Growth Factor (NGF; 10 ng/ml) and basic Fibroblast Growth Factor (FGFb; 5 ng/ml) and the cells were intoxicated under the same conditions.

At the end of the two incubation periods (6 and 24 hours) the cell layers were fixed and marked with a anti-68- and 200 kD neurofilament monoclonal antibody (DAKO M0762) and then developed using a mouse anti-immunoglobulin goat antibody conjugate Alexia fluor 488 (Interchim A-11029). Controls without primary antibody were performed. All the controls were negative (no non-specific labelling). After extensive washing with PBS the preparations were observed under epi-fluorescence (Nikon Diaphot 300 microscope).

2 images were obtained for each culture well (4 wells per experimental condition) using a Nikon DXM1200F camera controlled by LUCIA 6.0 software.

All the images were obtained under the same conditions and with identical camera settings.

The densities of the networks of extensions marked with anti-neurofilament antibody were examined using LUCIA 6.0 software. Initial image processing made it possible to increase the intensity of the specific marking on the extensions. Areas in which marking was positive were binarised and the percentage marking per image was determined (marked surface area/total surface area examined).

1.4. Product Investigated
Etifoxine (6-chloro-2-ethylamino-4-methyl-4-phenyl-4H-[3,1]benzoxazine hydrochloride) was dissolved in a concentration of 100 mM in DMSO and then diluted successively in culture medium (DMSO concentration ≦0.1%, v/v).

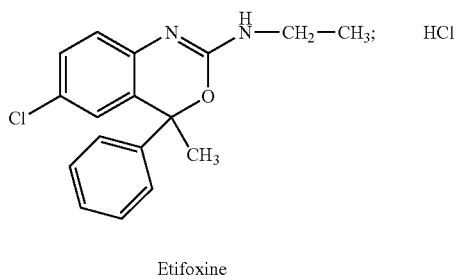

Etifoxine 1.5. Expression and Statistical Analysis of the Results

The results (mean values±standard error with respect to the mean (SEM) were expressed as percentage marking per microscope field (n=8 measurements/culture conditions). 2-factor analysis of variance (Etifoxine and glutamate), followed by the Student Newman-Keuls multiple comparisons test was used for statistical comparison of the results.

The results obtained with the positive control (FGF) were compared with the controls using Student's t test or the Mann and Whitney test as appropriate. The significance threshold was set at p<0.05 (SigmaStat software—V3.1, SPSS inc).

2. Results 2.1 Cytotoxicity of Etifoxine

A first experiment was carried out (conventional test used to measure the level of cell survival) in order to investigate the cytotoxicity of etifoxine in relation to cortical neurones in the presence of astrocytes in culture and thus to determine the maximum non-toxic concentration of etifoxine.

Visual examination carried out with a microscope after 48 hours incubation showed neurone mortality at a concentration of 33 and 100 μM of etifoxine, whereas astrocyte mortality was observed at a concentration of 100 μM. The etifoxine concentrations adopted for the investigation proper were 1, 3 and 10 μM.

2.2 Effects of Etifoxine on Neurofilament Density in the Presence of Glutamate after 6 Hours Incubation (FIG. 1)

In the control culture medium (without glutamate), etifoxine increased the density of marked neurofilaments in a dose-dependent way with a statistically significant effect at a dose of 10 μM.

In concentrations of 2 and 10 mM glutamate reduced the density of neurofilaments in a statistically significant way. In concentrations of 3 and 10 μM, etifoxine and FGF opposed the decrease in density of neurofilaments induced by glutamate in a statistically significant way.

Figure 2:
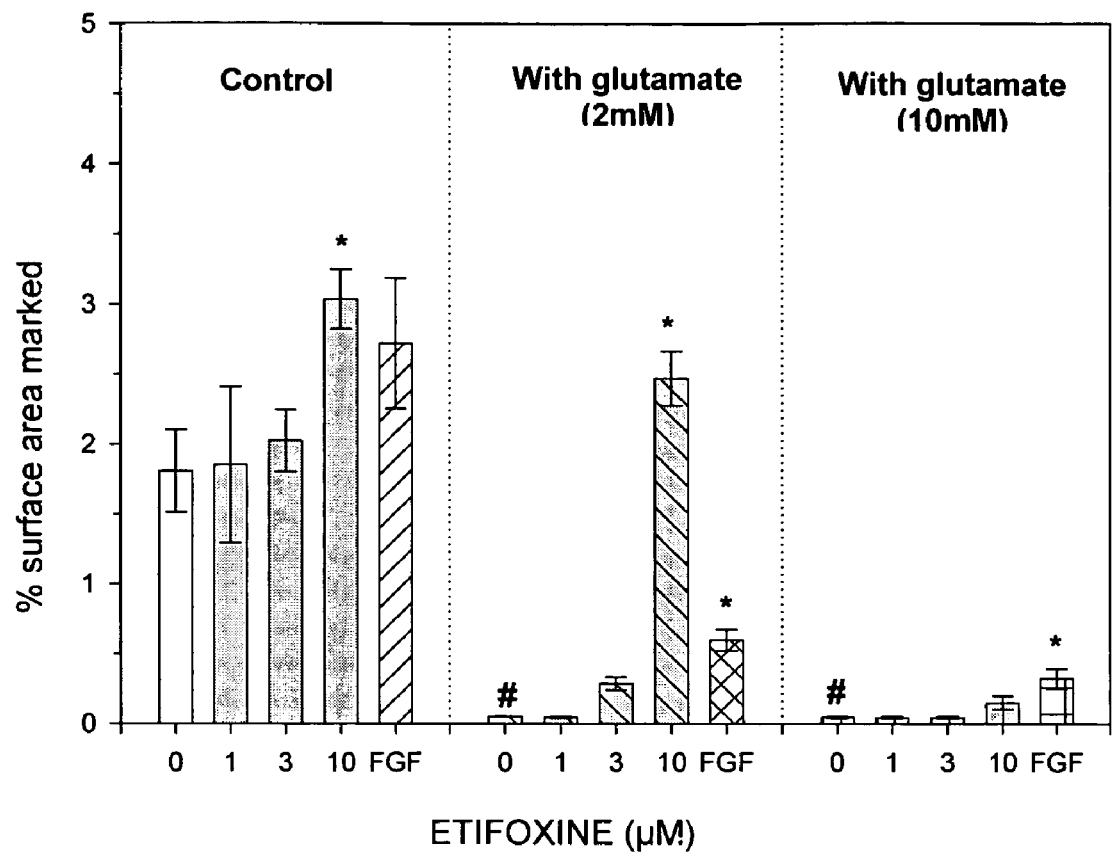
FIG. 2

2.3 Effects of Etifoxine on Neurofilament Density in the Presence of Glutamate after 24 Hours (FIG. 2)

As previously, in control culture medium etifoxine increased the density of neurofilaments at a dose of 10 μM in a statistically significant way. The concentrations of 1 and 3 μM were without effect.

At concentrations of 2 and 10 mM glutamate significantly reduced the marking of neurofilaments, which was close to 0.

Etifoxine in a concentration of 10 μM and FGF opposed the effects of 2 mM of glutamate in a statistically significant way.

The results reveal that etifoxine has an effect on neurone growth or a neurotrophic effect as shown by the increase in the density of the neurofilament networks in the control culture after 6 and 24 hours incubation.

In addition to this they also show that etifoxine has a neuroprotector effect after intoxication by glutamate. In fact, etifoxine, like growth factors, opposes the reduction in neurofilament networks induced by an excess of glutamate.

Example 2

Evaluation of the Neuroprotector Effects of Desethyl-Etifoxine in Mixed Cultures of Rat Cortical Neurones and Astrocytes in the Presence of Excess Glutamate The procedure in Example 1 was applied to an active metabolite of etifoxine, namely desethyl-etifoxine (2-amino-6-chloro-4-methyl-4-phenyl-4H-[3,1]benzoxazine), which was dissolved in DMSO to a concentration of 100 mM and then successively diluted with culture medium (DMSO concentration ≦0.1%, v/v).

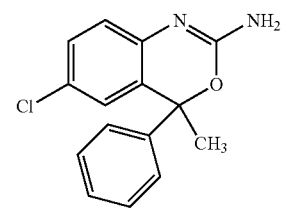

Desethyl-etifoxine

Cytotoxicity of Desethyl-Etifoxine

Visual examination carried out under a microscope after 48 hours incubation showed neurone mortality at concentrations of 33 and 100 μM of desethyl-etifoxine, whereas astrocyte mortality was observed at a concentration of 100 μM. The desethyl-etifoxine concentrations adopted for the investigation proper were 1, 3 and 10 μM.

Figure 3:
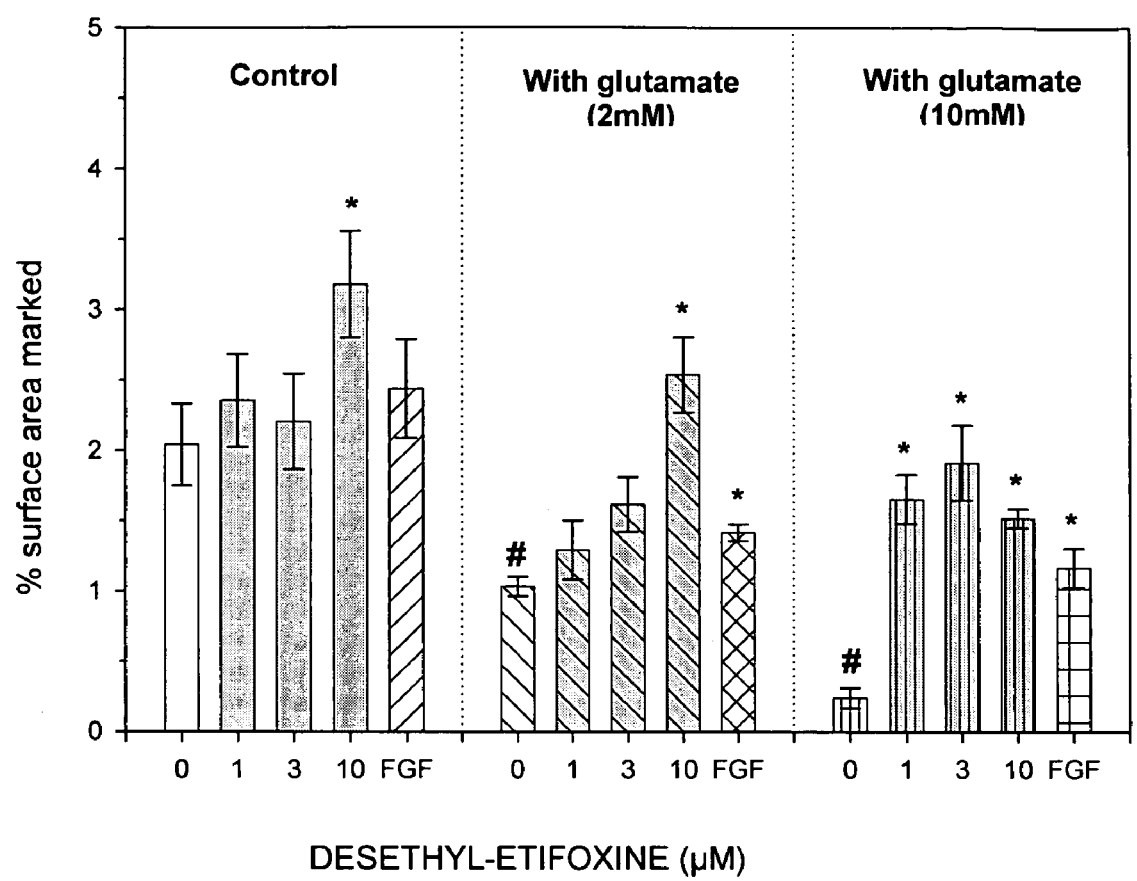
FIG. 3

Effects of Desethyl-Etifoxine on Neurofilament Density in the Presence of Glutamate after 6 Hours Incubation (FIG. 3)

In control culture medium (without glutamate), desethyl-etifoxine increased the density of labelled neurofilaments in a statistically significant way at a dose of 10 μM. Glutamate in a concentration of 2 mM reduced the density of neurofilaments in a statistically significant way. Only the concentration of 10 μM of desethyl-etifoxine opposes the effect of glutamate. On the other hand, desethyl-etifoxine in concentrations of 1, 3 and 10 μM opposes the decrease in the density of marked neurofilaments induced by 10 μM of glutamate in a statistically significant way.

Example 3

Protective Effect of Etifoxine in 3 Models of Hypoxia in Mice and Rats

Many pathological situations, such as epileptic crises or cerebrovascular accidents, take the form of local or general hypoxia of the nervous tissues, resulting in their partial or total destruction, in particular through neurone death. In animals placed in conditions of severe hypoxia the destruction of nervous tissue rapidly leads to death of the animal. The effects of etifoxine on the survival time of mice or rats placed in a situation of hypoxia was therefore investigated in order to evaluate its neuroprotective effectiveness.

1. Material and Methods
1.1 Hypobaric Hypoxia in Mice
Animals

NMRI male mice from Janvier weighing between 25 and 30 grams were used after acclimatisation in the animal house for at least 7 days (t°=22±2° C.; humidity 50±20%; feed UAR "A04" SAFE (Augy, France) and tap water ad libitum; 12 hour night and day cycle (light from 7 a.m. to 7 p.m.).
Protocol The unfasting rats were distributed at random into lots of 10.

The protocol of Nakaniski et al. (1973) Life Sciences, 13, 467-474 was adapted for the purposes of the model.

Each mouse was placed in a dessicator (hermetically sealed enclosure) in which atmospheric pressure was reduced from 760 to 160 mmHg using a water pump. This pressure reduction was carried out in one minute and caused death of the control animals in approximately 1 minute.

The survival time of the animal, which corresponded to the difference between the time to death of the mouse assessed by respiratory arrest less the time required to induce the hypoxia was then noted.

The products under investigation were administered intraperitoneally (i.p.) (0.1 ml/10 g), 30 minutes before inducing hypobaric hypoxia, or orally (0.1 ml/10 g p.o.) 1 hour before hypoxia.
1.2 KCN Hypoxia (i.p.) in Mice
Animals CD1 male mice from Charles River weighing between 20 and 25 grams were used after acclimatisation in the animal house for at least 7 days (t°=22±2° C.; humidity 50±20% feed UAR "A04"; 12 hour night and day cycle (light from 7 a.m. to 7 p.m.)
Protocol The unfasting mice were subdivided into lots of 10 at random.

Each mouse received a freshly prepared solution of potassium cyanide (KCN) in 0.9% NaCl (1.5 mg/ml) intraperitoneally (i.p.) (0.1 ml/10 g). This was equivalent to a dose of 15 mg/kg of KCN which caused death of the control animals within a few minutes.

The time to death for each mouse, assessed by cardiac arrest, was noted.

The products under investigation were administered intraperitoneally (i.p.) (0.1 ml/10 g), 30 minutes before the injection of KCN, or orally (0.1 ml/10 g p.o.) 1 hour before the KCN.
1.3 KCN (i.v.) Hypoxia in Rats
Animals Wistar male rats from Janvier weighing between 180 and 200 grams were used after acclimatisation in the animal house for at least 7 days (t°=22±2° C.; humidity 50±20%; feed UAR "A04" SAFE (Augy, France); 12 hour night and day cycle (light from 7 a.m. to 7 p.m.).
Protocol The unfasting rats were subdivided into lots of 10 at random.

The protocol was adapted from after Lamar et al. (1988) *Drug Develop. Res.*, 14, 297-304.

Each rat received a freshly prepared solution of potassium cyanide (KCN) in 0.9% NaCl (4 mg/ml) intravenously (i.v.) (0.1 ml/100 g). This was equivalent to a dose of 4 mg/kg of KCN which caused death of the control animals within a few minutes.

The time to death was noted for each rat, assessed by cardiac arrest.

The products under investigation were administered intraperitoneally (i.p.) (0.5 ml/100 g), 30 minutes before the injection of CN, or orally (0.5 ml/100 g p.o.) 1 hour before the KCN.
1.4 Products Etifoxine hydrochloride was dissolved in 1% Tween 80. The potassium cyanide (Merck) was dissolved in 0.9% NaCl.
1.5 Statistics The statistical test used was a one-factor analysis of variance to determine the treated groups, which differed from the control group receiving the vehicle, at a threshold of 5%.
2. Results
2.1 Hypobaric Hypoxia in Mice Pressure reduction to bring about hypobaric hypoxia resulted in death of the mice not receiving treatment or receiving the vehicle liquid within 40 to 60 seconds.

Figure 4A:
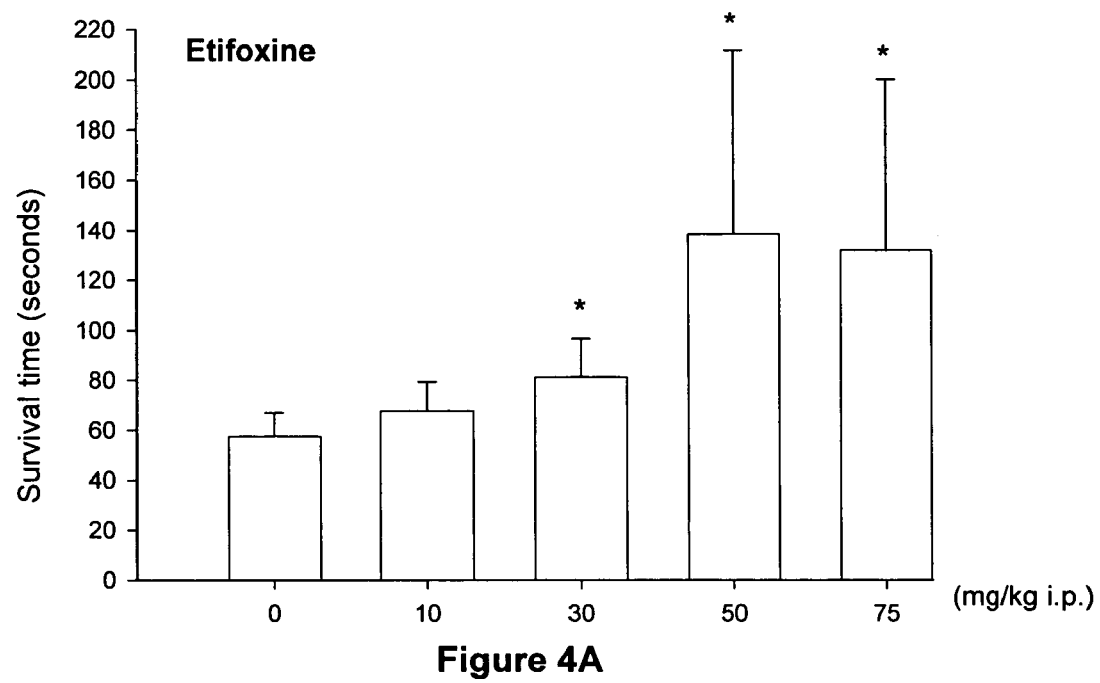
FIG. 4A and FIG. 4B
Figure 4B:
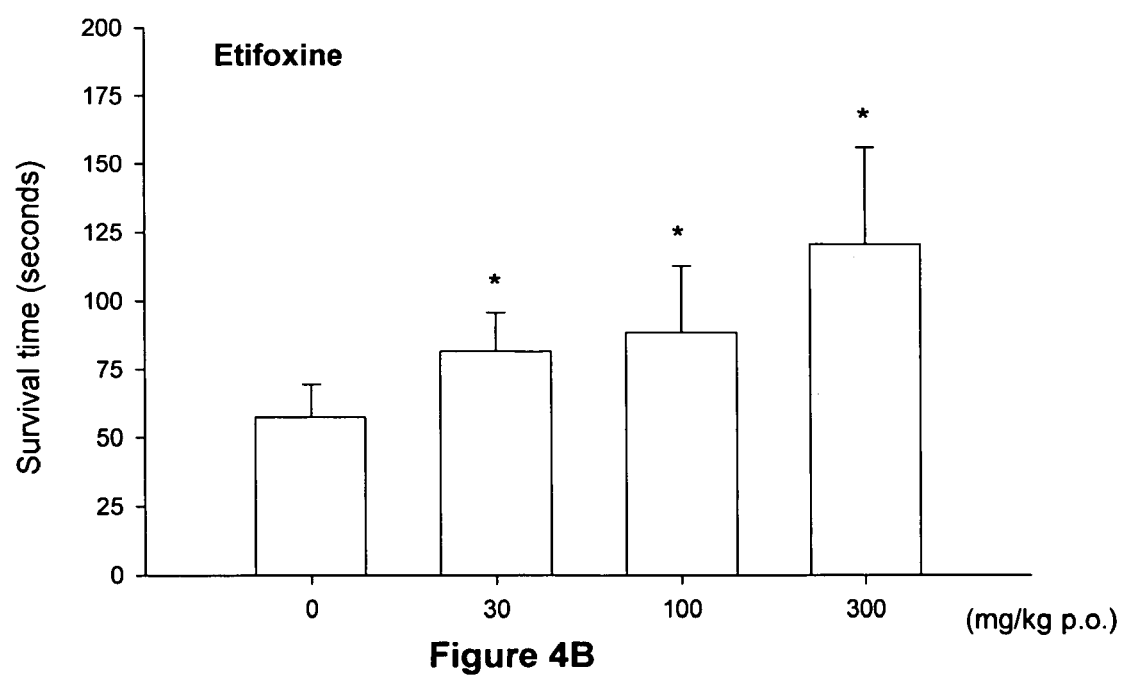

Etifoxine significantly increased the time to death over 30 mg/1 kg i.p. or p.o. (Table 1 and FIGS. 4A-4B).

TABLE 1

Effects of etifoxine on survival time in hypobaric hypoxia induced by reducing atmospheric pressure to 160 mmHg in mice (n number of animals, m mean, sem standard deviation from the mean).

| Route | Dose (mg/kg) | n | Survival time in seconds (m ± sem) | Percentage variation | ANOVA statistical test |
|---|---|---|---|---|---|
| i.p. | 0 | 20 | 57.5 ± 2.0 | | |
| | 3 | 10 | 64.5 ± 3.4 | +12 | ns |
| | 10 | 19 | 66.1 ± 3.0 | +15 | ns |
| | 30 | 19 | 81.8 ± 4.6 | +42 | p < 0.05 |
| | 50 | 10 | 138.5 ± 23.3 | +141 | p < 0.05 |
| | 75 | 10 | 132.0 ± 21.6 | +130 | p < 0.05 |
| p.o. | 0 | 20 | 55.5 ± 2.3 | | |
| | 30 | 10 | 81.5 ± 4.5 | +47 | p < 0.05 |
| | 100 | 20 | 95.3 ± 5.6 | +72 | p < 0.05 |
| | 200 | 10 | 99.5 ± 2.7 | +79 | p < 0.05 |
| | 300 | 20 | 115.5 ± 8.6 | +108 | p < 0.05 |

2.2 KCN (i.p.) Hypoxia in Mice

Administration of 15 mg/kg i.p. of KCN resulted in death of the mice without treatment or receiving the liquid vehicle within 90 to 120 seconds.

Figure 5A:
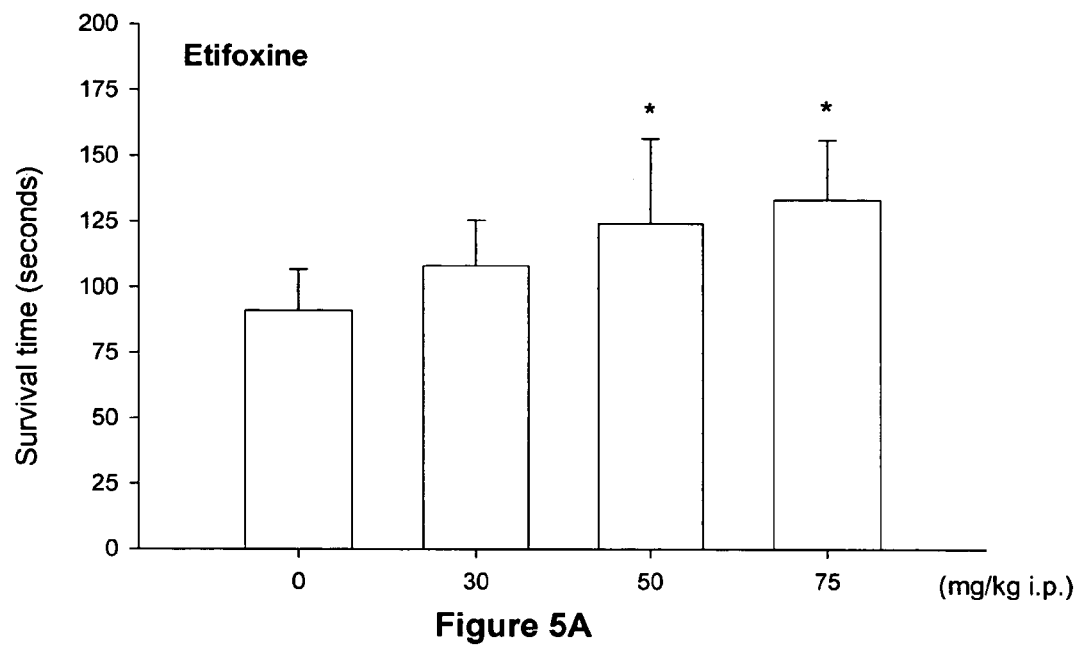
FIG. 5A and FIG. 5B
Figure 5B:
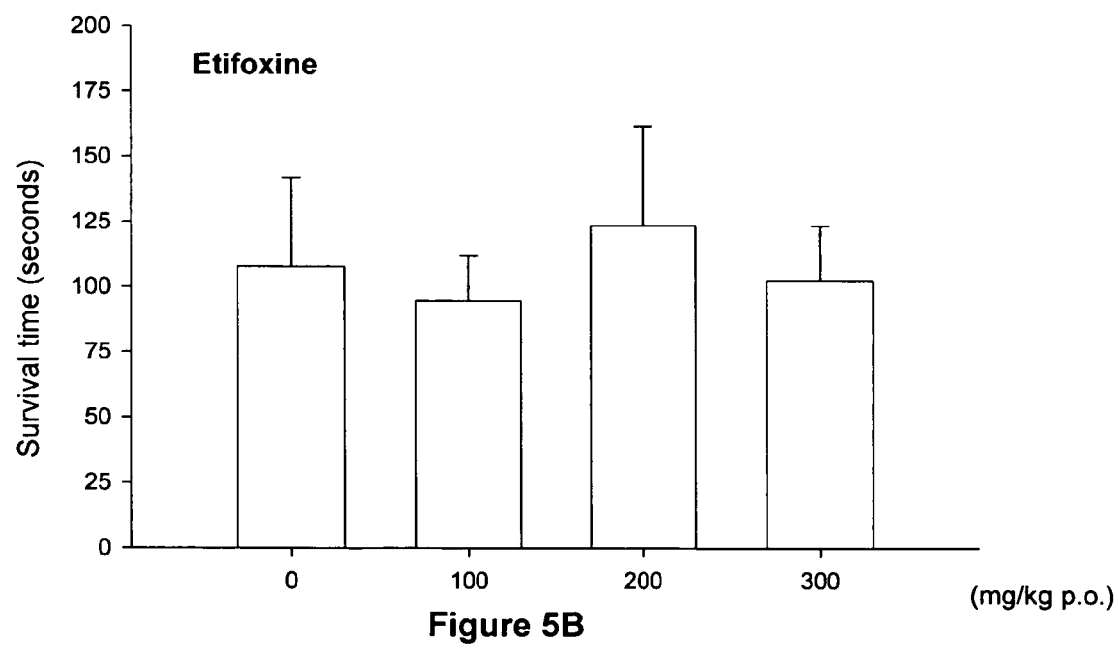

Etifoxine significantly increased the time to death over 50 mg/kg i.p., but did not significantly affect survival time following oral administration (Table 2 and FIGS. 5A-5B).

TABLE 2

Effects of etifoxine on survival time in histotoxic hypoxia induced by potassium cyanide (15 mg/kg i.p.) in mice (n number of animals, m mean, sem standard deviation from the mean).

| Route | Dose | n | Survival time in seconds (m ± sem) | Percentage variation | ANOVA statistical test |
|---|---|---|---|---|---|
| i.p. | 0 | 19 | 106 ± 9 | | |
| | 3 | 19 | 122 ± 7 | +15 | ns |
| | 10 | 20 | 113 ± 5 | +7 | ns |
| | 30 | 18 | 129 ± 11 | +22 | ns |
| i.p. | 0 | 19 | 91 ± 4 | | |
| | 30 | 16 | 108 ± 4 | +19 | ns |
| | 50 | 18 | 124 ± 8 | +36 | p < 0.05 |
| | 75 | 17 | 133 ± 6 | +46 | p < 0.05 |
| p.o. | 0 | 9 | 108 ± 11 | | |
| | 100 | 9 | 94 ± 6 | −13 | ns |
| | 200 | 10 | 123 ± 12 | +14 | ns |
| | 300 | 10 | 102 ± 7 | −6 | ns |

2.3 KCN Hypoxia (i.v.) in Rats

Administration of 4 mg/kg i.v. of KCN resulted in death of the untreated rats or rats receiving the liquid vehicle in 50 to 60 seconds.

Figure 6A:
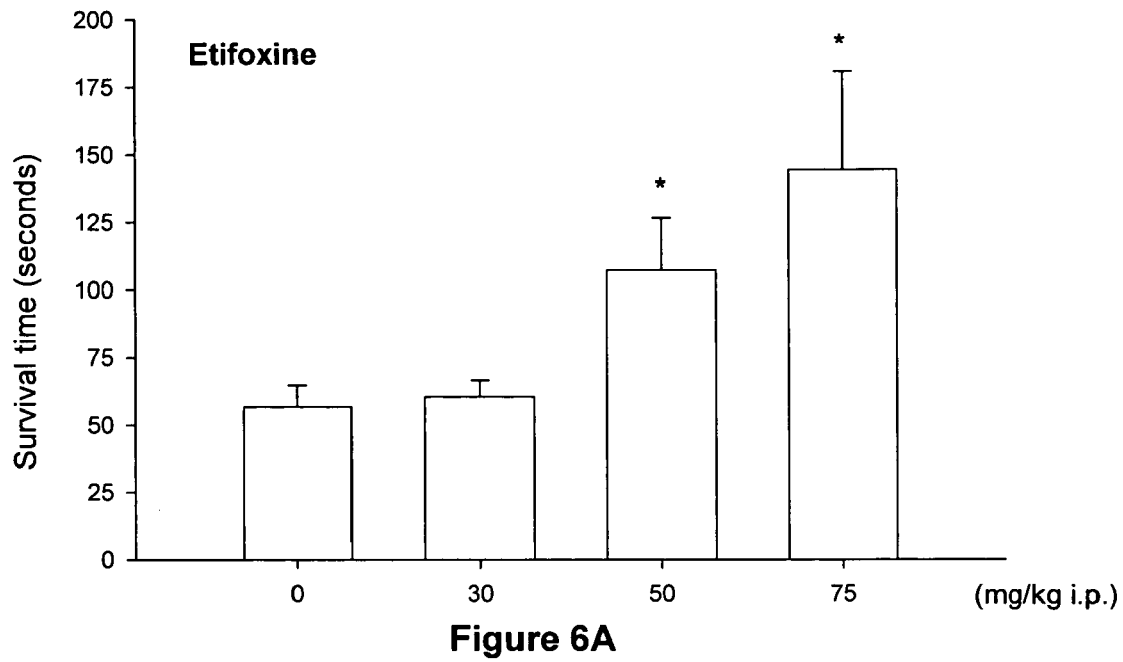
FIG. 6A and FIG. 6B
Figure 6B:
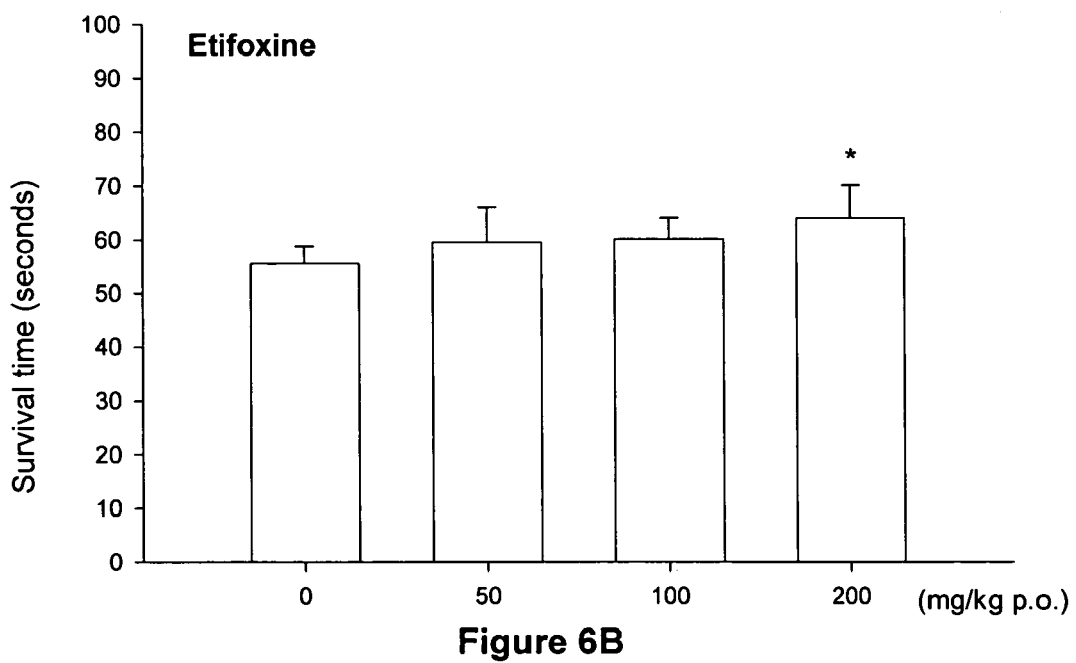

Etifoxine significantly increased the time to death from 50 mg/kg i.p. and 200 mg/kg p.o. (Table 3 and FIGS. 6A 6B).

TABLE 3

Effects of etifoxine on survival time in histotoxic hypoxia induced by potassium cyanide (4 mg/kg i.v.) in rats (n number of animals, m mean, sem standard deviation from the mean).

| Route | Dose | n | Survival time in seconds (m ± sem) | Percentage variation | ANOVA statistical test |
|---|---|---|---|---|---|
| i.p. | 0 | 10 | 56.6 ± 2.6 | | |
| | 30 | 10 | 60.3 ± 2.0 | +7 | ns |
| | 50 | 10 | 107.3 ± 6.1 | +90 | p < 0.05 |
| | 75 | 10 | 144.3 ± 11.5 | +155 | p < 0.05 |
| p.o. | 0 | 9 | 55.4 ± 1.1 | | |
| | 50 | 10 | 59.5 ± 2.1 | +7 | ns |
| | 100 | 10 | 60.1 ± 1.2 | +8 | ns |
| | 200 | 10 | 63.9 ± 2.0 | +15 | p < 0.05 |

Example 4

The procedure in Example 3 was applied to desethyl-etifoxine which was dissolved in 1% Tween 80.

1 Hypobaric Hypoxia in Mice

Figure 7A:
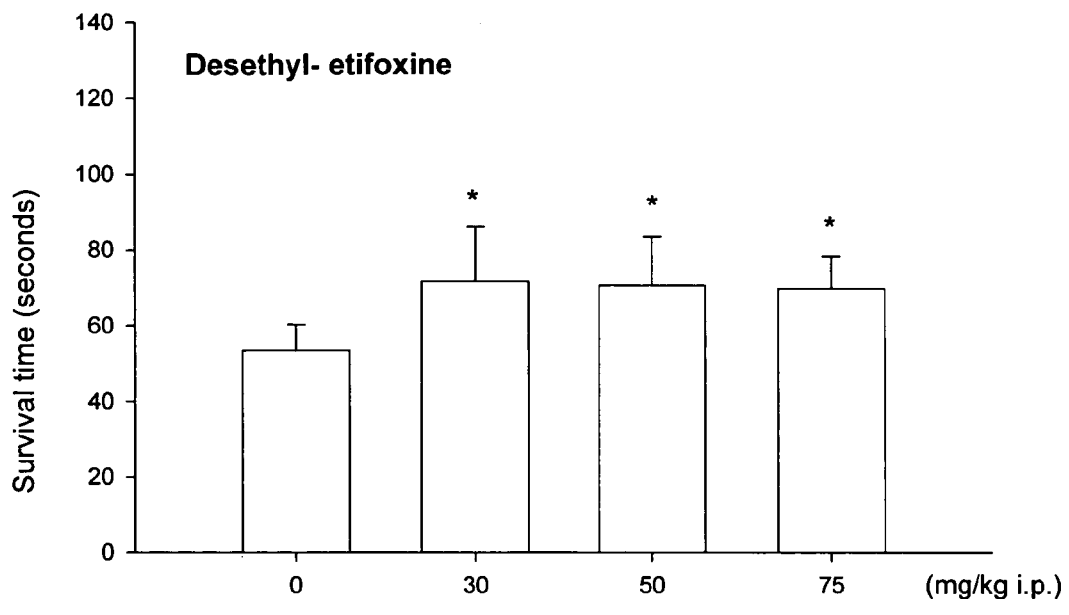
FIG. 7A and FIG. 7B
Figure 7B:
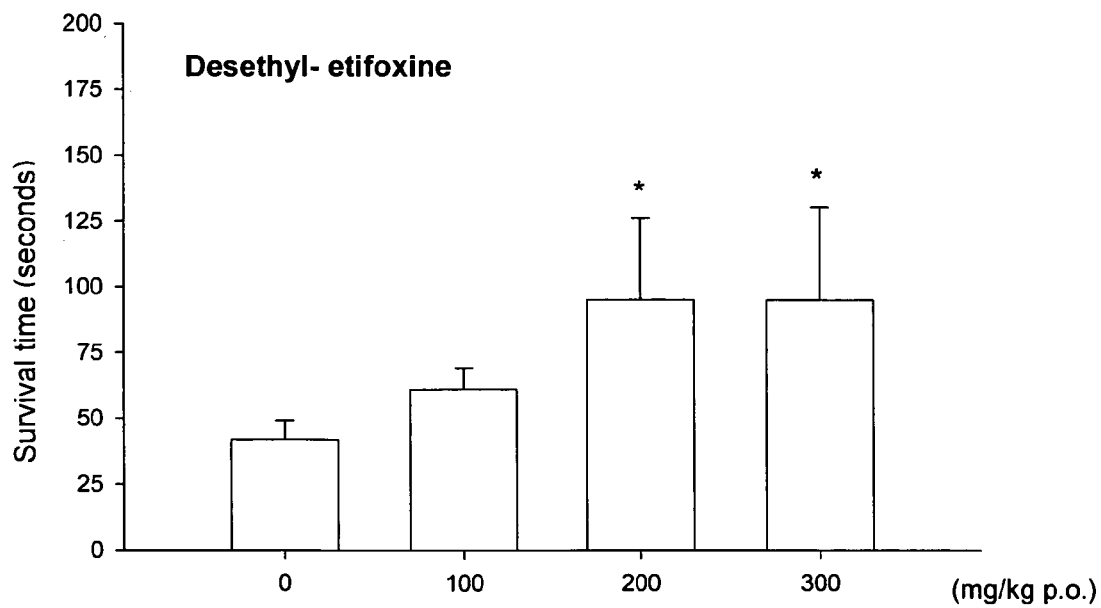

Desethyl-etifoxine showed anti-hypoxic activity over 30 mg/kg i.p. In oral administration it gave rise to a significant increase in survival time from 200 mg/kg (Table 4 and FIGS. 7A-7B).

TABLE 4

Effects of desethyl-etifoxine on survival time in hypobaric hypoxia induced by reducing atmospheric pressure to 160 mmHg in mice (n number of animals, m mean, sem standard deviation from the mean).

| Route | Dose | n | Survival time in seconds (m ± sem) | Percentage variation | ANOVA statistical test |
|---|---|---|---|---|---|
| i.p. | 0 | 10 | 53.5 ± 2.2 | | |
| | 30 | 9 | 71.7 ± 4.8 | +34 | p < 0.05 |
| | 50 | 9 | 70.7 ± 4.3 | +32 | p < 0.05 |
| | 75 | 10 | 69.8 ± 2.7 | +30 | p < 0.05 |
| p.o. | 0 | 10 | 42.0 ± 2.3 | | |
| | 100 | 10 | 61.0 ± 2.6 | +45 | ns |
| | 200 | 10 | 94.9 ± 9.9 | +126 | p < 0.05 |
| | 300 | 10 | 94.8 ± 11.2 | +126 | p < 0.05 |

2 KCN (i.p.) Hypoxia in Rats

Figure 8A:
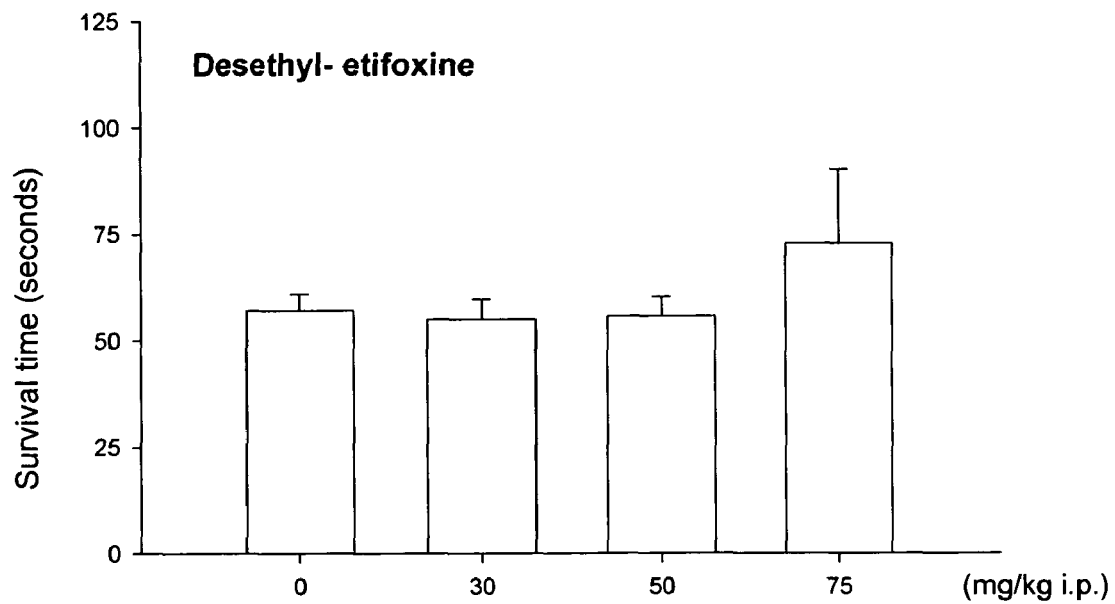
FIG. 8A and FIG. 8B
Figure 8B:
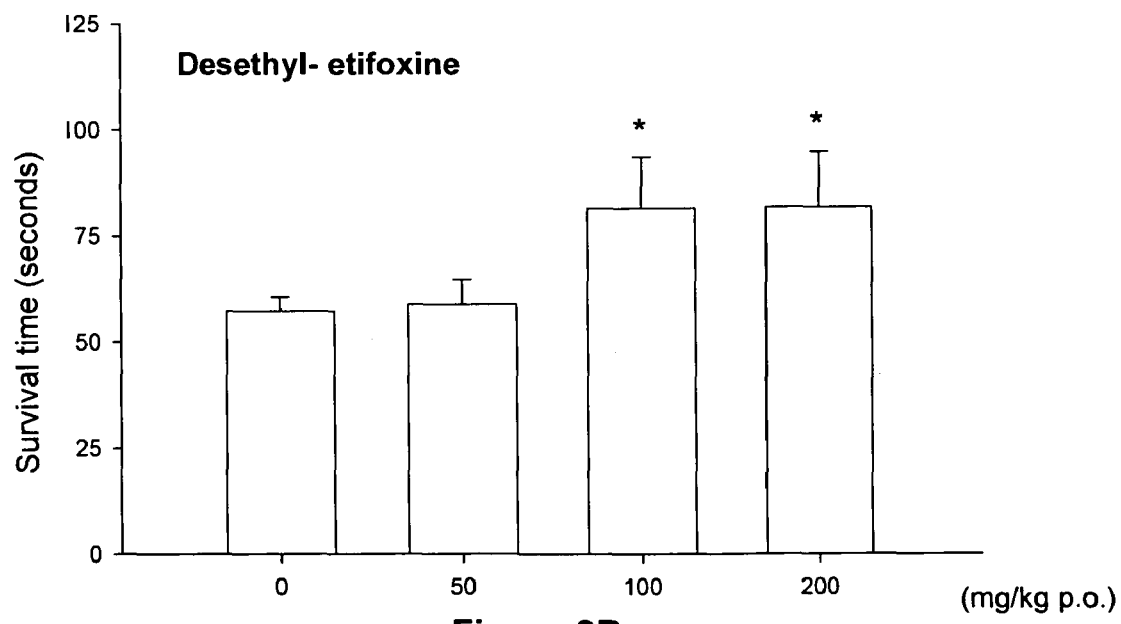
Figure 9:
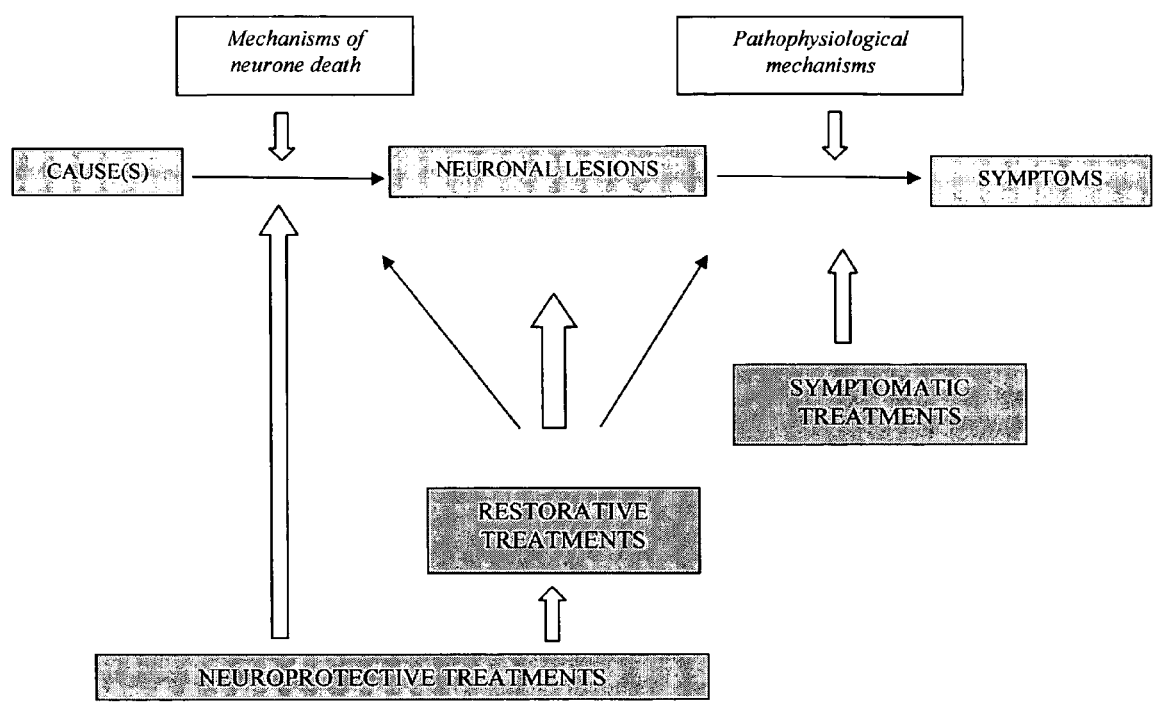
FIG. 9

In this test, desethyl-etifoxine increased survival time in a non-significant manner at 75 mg/kg i.p., because of high variability. In oral administration it showed anti-hypoxic activity over 100 mg/kg p.o. (Table 5 and FIGS. 8A-8B).

TABLE 5

Effects of desethyl-etifoxine on survival time in histotoxic hypoxia induced by potassium cyanide (4 mg/kg i.p.) in rats (n number of animals, m mean, sem standard deviation from the mean).

| Route | Dose | n | Survival time in seconds (m ± sem) | Percentage variation | ANOVA statistical test |
|---|---|---|---|---|---|
| i.p. | 0 | 10 | 57.1 ± 1.2 | | |
| | 30 | 10 | 55.0 ± 1.5 | −4 | ns |

TABLE 5-continued

Effects of desethyl-etifoxine on survival time in histotoxic hypoxia induced by potassium cyanide (4 mg/kg i.p.) in rats (n number of animals, m mean, sem standard deviation from the mean).

| Route | Dose | n | Survival time in seconds (m ± sem) | Percentage variation | ANOVA statistical test |
|---|---|---|---|---|---|
| | 50 | 10 | 55.6 ± 1.5 | −3 | ns |
| | 75 | 10 | 72.7 ± 5.5 | +27 | ns |
| p.o. | 0 | 10 | 57.3 ± 1.0 | | |
| | 50 | 10 | 58.8 ± 1.9 | +3 | ns |
| | 100 | 10 | 81.3 ± 3.8 | +42 | p < 0.05 |
| | 200 | 10 | 81.7 ± 4.1 | +43 | p < 0.05 |

The invention claimed is:

1. A method for treating neurone deteriorations in an individual, comprising administering to said individual a therapeutically effective quantity of at least one compound having neuroprotective activity selected from the group consisting of formula (III):

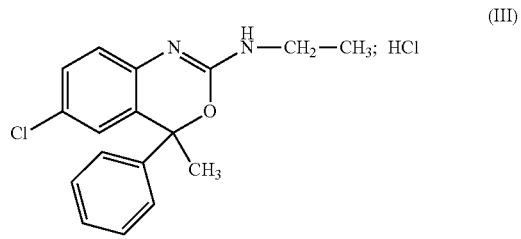

(III)

and formula (IV):

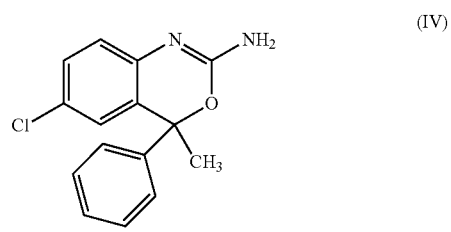

(IV)

or their pharmaceutically acceptable salts;
in which neurone deteriorations are linked to diseases selected from the group consisting of:
epilepsy,
ischaemic cerebral vascular accidents,
neuropathic diseases selected from the group consisting of polyneuropathy, alcoholic polyneuropathy, toxic or drug-induced neuropathy, vincristine-induced neuropathy, neuropathy associated with a metabolic disturbance, neuropathy associated with diabetes, neuropathy associated with an inflammatory process, neuropathy associated with Guillain-Barre syndrome, infectious neuropathic diseases, Herpes zoster, and radiculoneuropathic diseases,
multiple sclerosis,
amyotrophic lateral sclerosis,
schizophrenia,
depression,
brain tumours,
Parkinson's disease
Alzheimer's disease, and
Pick's disease.

2. The method of claim 1, wherein the compound is administered to the individual at a unit dose from approximately 50 mg to approximately 1500 mg.

3. The method of claim 1, wherein the compound is administered to the individual at a dosage from approximately 50 mg/d to approximately 1500 mg/d.

4. The method of claim 1, wherein the compound is administered by the oral route.

5. The method of claim 1, wherein the compound is administered to the individual in the form of a powder, patches, capsules or sachets.

6. The method of claim 1, wherein the compound is simultaneously, separately, or sequentially administered with at least one additional compound intended to treat the diseases.

7. The method of claim 1, wherein the compound is administered to the individual at a unit dose from approximately 150 to 200 mg.

8. The method of claim 1, wherein the compound is administered to the individual at a dosage from approximately 150 mg/d to approximately 200 mg/d.

9. A method for promoting neurone growth in an individual, comprising administering to said individual an effective quantity of at least one compound selected from the group consisting of formula (III):

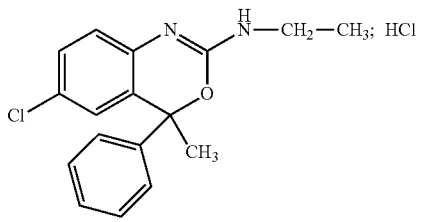

(III); and formula (IV):

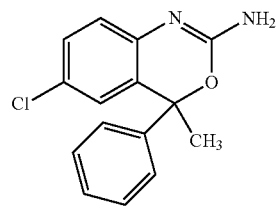

or their pharmaceutically acceptable salts.

* * * * *

UNITED STATES PATENT AND TRADEMARK OFFICE
CERTIFICATE OF CORRECTION

PATENT NO. : 8,338,410 B2
APPLICATION NO. : 11/488187
DATED : December 25, 2012
INVENTOR(S) : Verleye et al.

It is certified that error appears in the above-identified patent and that said Letters Patent is hereby corrected as shown below:

Title page, item (75) Inventors change:

"Margeny-les-Compeigne (FR)" to -- Margny-Les-Compiègne (FR) --

Signed and Sealed this
Second Day of April, 2013

Teresa Stanek Rea
*Acting Director of the United States Patent and Trademark Office*

UNITED STATES PATENT AND TRADEMARK OFFICE
CERTIFICATE OF CORRECTION

Page 1 of 1

PATENT NO. : 8,338,410 B2
APPLICATION NO. : 11/488187
DATED : December 25, 2012
INVENTOR(S) : Verleye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1378 days.

Signed and Sealed this
Eighteenth Day of November, 2014

Michelle K. Lee
*Deputy Director of the United States Patent and Trademark Office*